United States Patent
Weber et al.

(10) Patent No.: US 6,875,898 B2
(45) Date of Patent: Apr. 5, 2005

(54) PROCESS FOR PREPARING PHENOLS

(75) Inventors: Manfred Weber, Haltern (DE); Reinhard Sigg, Mari (DE); Michael Lausmann, Gladbeck (DE); Siegmund Greschek, Gladbeck (DE)

(73) Assignee: Ineos Phenol GmbH & Co. KG, Gladbeck (DE)

( * ) Notice: Subject to any disclaimer, the term of this patent is extended or adjusted under 35 U.S.C. 154(b) by 51 days.

(21) Appl. No.: 10/408,152

(22) Filed: Apr. 4, 2003

(65) Prior Publication Data

US 2003/0220528 A1 Nov. 27, 2003

Related U.S. Application Data

(60) Provisional application No. 60/379,153, filed on May 8, 2002.

(30) Foreign Application Priority Data

Apr. 4, 2002 (EP) ............................................. 02007637

(51) Int. Cl.$^7$ ................................................ C07C 37/08
(52) U.S. Cl. ...................................................... 568/798
(58) Field of Search ......................................... 568/798

(56) References Cited

U.S. PATENT DOCUMENTS

| 2,744,143 | A | * | 5/1956 | Filar ........................... 568/798 |
| 3,692,845 | A | | 9/1972 | Chemma et al. |
| 4,283,568 | A | | 8/1981 | Pujado |
| 6,066,767 | A | | 5/2000 | Zakoshansky et al. |
| 6,630,608 | B2 | * | 10/2003 | Tanger et al. ................ 568/754 |

* cited by examiner

*Primary Examiner*—Michael L. Shippen
(74) *Attorney, Agent, or Firm*—Knobbe, Martens, Olson & Bear, L.L.P.

(57) ABSTRACT

The present invention relates to a process for preparing phenols by adding an aqueous base to the reaction product from the acid-catalyzed cleavage of alkylaryl hydroperoxides while maintaining a homogeneous phase prior to the work-up of the product.

16 Claims, No Drawings

PROCESS FOR PREPARING PHENOLS

RELATED APPLICATIONS

This Application claims the benefit of priority of the U.S. Provisional Application No. 60/379,153 filed May 8, 2002, and European Patent Application EP 02 007 637.8 filed Apr. 4, 2002, which are hereby expressly incorporated by reference in their entireties.

BACKGROUND OF THE INVENTION

1. Field of the Invention

The present invention relates to an improved process for preparing phenols.

2. Description of the Related Art

The process of acid-catalyzed cleavage of cumene hydroperoxide into phenol and acetone has been of particular industrial importance for a long time. In the preparation of phenol from cumene by the Hock process, cumene is oxidized to cumene hydroperoxide (CHP) in a first reaction step, known as oxidation, and the CHP is subsequently concentrated to from 65 to 90% by weight in a vacuum distillation, known as concentration. In a second reaction step, known as cleavage, the CHP is cleaved into phenol and acetone by action of an acid, usually sulfuric acid. In this step, the dimethyl phenyl carbinol (DMPC) formed in the oxidation is partly cleaved in an equilibrium reaction into α-methylstyrene (AMS) and water, while a further part of the DMPC reacts with CHP to form dicumyl peroxide (DCP); the rest remains in the cleavage product. After neutralization of the cleavage product, this product mixture is usually worked up by distillation.

In the cleavage, part of the AMS or of the DMPC forms high boilers (dimers, cumylphenols, bisphenols) which are discharged as residue in the distillation. The AMS still present after the neutralization, is hydrogenated to cumene in the distillation and is returned to the oxidation. DMPC which is not reacted in the cleavage ends up as high boiler in the residue; part of it reacts further in the hot phenol columns to form AMS from which high-boiling secondary components are once again formed. DCP is stable at customary cleavage temperatures (50–70° C.). It decomposes thermally in the hot phenol columns forming, in our experience, o-cresol, at least in part. On the other hand, in the presence of acid, DCP can be cleaved into phenol, acetone and AMS at temperatures above 80° C. It is therefore obvious for the remaining DMPC and the DCP formed in the cleavage to be reacted completely immediately after the cleavage by means of a targeted increase in the temperature in the presence of the acid used as catalyst in the cleavage. In this way, DMPC is largely converted into AMS and DCP is converted virtually completely into phenol, acetone and likewise AMS.

Such a thermal after-treatment of the cleavage product has already been described in U.S. Pat. No. 2,757,209, where temperatures above 100° C., specifically from 110 to 120° C., were employed. The objective of this thermal after-treatment was the complete dehydration of DMPC to AMS. On the other hand, U.S. Pat. No. 4,358,618 describes a thermal after-treatment which has the aim of converting all of the DCP formed in the cleavage into phenol, acetone and AMS; in that patent, temperatures of 120 and 150° C. are employed. U.S. Pat. No. 5,254,751 describes a thermal after-treatment which has the same objective as that in U.S. Pat. No. 4,358,618 and uses temperatures of from 80 to 110° C. Finally, in DE 197 55 026 A1, the after-treatment is carried out in a temperature range above 150° C. In all these processes known from the prior art, the thermally treated product is subsequently cooled to (customarily) 40° C. by means of a cooler, then neutralized and, after separating off a salt-containing aqueous phase, worked up by distillation.

A disadvantage of the above-described processes is that hydroxyacetone and other carbonyl compounds such as acetaldehyde, propionic aldehyde and phenyl propanal are formed as by-products and these, firstly, make the work-up of the reaction product difficult and, secondly, hydroxyacetone in particular reacts with phenol in specific phenol purification processes to form high boilers, thus leading to undesirable losses of phenol. It would therefore be desirable to reduce the content of hydroxyacetone and other impurities in the cleavage product.

U.S. Pat. No. 6,066,767 describes a process for removing hydroxyacetone and other carbonyl compounds from the product of the cleavage of cumene hydroperoxide. For this purpose, the reaction product of the cumene hydroperoxide cleavage is extracted with an aqueous salt solution in a temperature range of 15–80° C. to remove hydroxyacetone, inter alia. The loaded extractant is subsequently treated with a base in a separate reactor to convert hydroxyacetone into condensation products. The extractant which has been treated in this way is returned to the extraction stage where the condensation products go into the organic phase and are then separated off in the work-up of the phenol- and acetone-containing organic phase. The examples show that, despite the very complicated apparatus employed for purification by extraction and subsequent reaction of the extracted hydroxyacetone, the organic product phase which is passed to further work-up for the isolation of phenol still contains 500–800 ppm of hydroxyacetone.

Furthermore, it has been discovered that the sodium hydroxide still present in the extractant will react with the phenol present in the organic phase of the cleavage product when the extractant is returned to the extraction stage. The basic strength of sodium phenolate formed thereby is too low to achieve a reasonable reaction rate for the conversion of hydroxyacetone in the aqueous phase after extraction. Therefore it is mandatory in the process disclosed in U.S. Pat. No. 6,066,767 to add fresh sodium hydroxide to the stage where the hydroxyacetone is converted to high-boilers. Thus an additional disadvantage of the process disclosed in U.S. Pat. No. 6,066,767 is, that fresh starting material like sodium hydroxide is consumed and wasted to a considerable extent contributing to undesired high operating costs for the prior art process.

In Vasileva, I. I. et al., 2000 *Neftepererab. Neftekhim., Moscow, Russ. Fed.*, 12:34–38 a process of extraction and conversion of hydroxyacetone from the product of cumene hydroperoxide cleavage similar to U.S. Pat. No. 6,066,767 is disclosed. The only disclosure additional to the teaching of U.S. Pat. No. 6,066,767 is that air can be introduced into the reactor where the aqueous extractant phase comprising hydroxyacetone is treated with added sodium hydroxide in order to increase the rate of conversion of hydroxyacetone. Therefore the process taught by Vasileva et. al. exhibits the same disadvantages as the process known from U.S. Pat. No. 6,066,767.

From US 2002-0183563 a process for preparing phenols, in which the pH of the reaction product from the acid-catalyzed cleavage of alkylaryl hydroperoxides is set to a value of at least 8 by addition of an basic aqueous solution at a temperature of at least 100° C. prior to the work-up of the product is known. Thereby an emulsion of the basic aqueous solution in the organic phase of the cleavage product is formed with the result that a high volume flow of a two-phase inhomogeneous mixture like in the process of U.S. Pat. No. 6,066,767 has to be processed. Furthermore, it has been discovered that under the reaction conditions described in US 2002-0183563 condensation products with acetone are formed resulting in losses of valuable products.

U.S. Pat. No. 4,283,568 describes a process for the recovery of phenol from a reaction mixture resulting from the acid cleavage of cumene hydroperoxide. Neutralization of the acidic reaction mixture is affected with an aqueous solution of sodium phenolate that is obtained a recycle stream in subsequent work-up stages of the process. The amount of added aqueous phenolate solution is such that a heterogeneous two-phase mixture is formed and the aqueous phase has to be separated from the organic phase in a settler.

In the process described in U.S. Pat. No. 3,692,845 non-aqueous component comprising a polyamine compound is added to the phenol obtained by the acid cleavage of cumene hydroperoxide in order to remove carbonyl bearing impurities.

SUMMARY OF THE INVENTION

It is therefore an object of the invention to provide a process for preparing phenols in which a reduction in the amount of undesirable impurities, in particular hydroxyacetone, prior to the work-up of the product can be achieved in a simple manner without losing valuable products.

This object has been achieved by a process for preparing phenols by adding an aqueous base to the reaction product from the acid-catalyzed cleavage of alkylaryl hydroperoxides while maintaining a homogeneous phase prior to the work-up of the product.

DETAILED DESCRIPTION OF THE PREFERRED EMBODIMENT

It has surprisingly been found that this simple procedure of adding an aqueous base to the reaction product from the acid-catalyzed cleavage of alkylaryl hydroperoxides while maintaining a homogeneous phase prior to the work-up of the product leads to a drastically reduced content of undesirable by-products, in particular hydroxyacetone, without the complicated apparatus described in the prior art cited being necessary. Furthermore, it has been discovered that the rate of conversion of undesired byproducts to high-boilers that can be easily separated in subsequent working-up stages is sufficiently high even at low temperatures, if the reaction product obtained from the acid-cleavage of alkylaryl hydroperoxides is maintained homogeneous. Surprisingly, also the overall selectivity of the process has not been compromised by addition of aqueous base in homogeneous phase, i.e. there is no appreciable reaction consuming desired products in the homogeneous phase after addition of the aqueous base. Furthermore, an additional advantage of the present invention is, that in addition to hydroxyacetone other undesired carbonyl functional by-products like aldehydes especially acetaldehyde, propionic aldehyde and phenyl propionic aldehyde that result in subsequent working-up stages in losses of the desired product or create problems in the separation of the desired products can be converted into high-boilers that can be easily separated without compromising the overall yield of desired product.

A further advantage compared to the teaching of the prior art, wherein either the organic phase of the reaction product resulting from alkylaryl hydroperoxide cleavage is extracted with an aqueous phase to remove hydroxyacetone or the addition of base results in an heterogeneous phase the total volume of process streams to be processed according to the present invention is reduced since an aqueous base is only added to the reaction product to the extent that an homogeneous phase is maintained. Thus operating and investment costs for the process of the present invention are considerable reduced while improving separation of undesired by-products.

According to a preferred embodiment of the present invention the aqueous base is selected from aqueous NaOH and aqueous phenoxide solutions, whereby aqueous phenoxide solutions are particularly preferred. When an aqueous NaOH solution is added it will result in increasing the phenoxide concentration of the homogeneous phase. When employing aqueous phenoxide solutions in the process of the present invention, advantageously an aqueous phenoxide solution recovered from at least one working-up stage of the process for preparing phenols can be used. Contrary to the processes of the prior art, wherein the conversion of by-products like hydroxyacetone is conducted in aqueous phase and therefore the addition of fresh sodium hydroxide is mandatory, the process of the present invention allows for the use of recovered process streams. Especially when conducting the base catalyzed conversion of carbonyl functional by-products like hydroxyacetone in homogeneous organic phase according to the present invention the base strength of phenoxides is sufficient to achieve an acceptable conversion rate. Thus the process of the present invention has an tremendous economic advantage over the prior art processes in that no fresh sodium hydroxide is required.

Preferably, the phenoxide is sodium phenolate and the aqueous sodium phenolate solution or the aqueous NaOH solution is added to the reaction product in an concentration and amount to result in an sodium phenolate concentration in the homogeneous phase of 0.2 to 2.5 wt.-%, preferably the sodium phenolate concentration in the homogeneous phase is 0.5 to 1 wt.-%.

The concentration of basic compound in the homogeneous phase of reaction product and aqueous base is adjusted by the amount and concentration of the aqueous base added to the reaction product. The only limitation is that after addition of the base the mixture of base and reaction product is still homogeneous. Especially the amount of water introduced by the addition of the aqueous base shall not exceed the solubility limit in the reaction product. The solubility limit of water in the reaction product will depend on the concentration of each of the components present in the reaction product. Thus the solubility limit may vary widely but is generally within the range of 5–12 wt.-%. A person skilled in the art can determine the solubility limit of water in a reaction product of a specific phenol process by standard means and can easily adjust amount and concentration of the aqueous base to be added without undue experimentation in order to fulfill the requirement of the present process that the reaction product is maintained in homogeneous phase.

As mentioned above, in the process of the present invention temperature is less critical as for example in the process disclosed in DE 101 10 392. Thus, in the present process the temperature of the homogeneous phase can be adjusted in a wide range of 20° C.–150° C., preferably 60° C.–120° C., most preferred 80° C. to less than 100° C.

According to a particularly preferred embodiment of the present invention an oxygen containing gas is introduced into the reaction product. Thereby the conversion rate of the carbonyl functional undesired by-products can be considerably increased. Consequently the temperature and/or the residence time prior to the work-up of the reaction product can be reduced. Thereby operation and investment costs of the present process can be further reduced.

Although Vasileva et al. already teach that by introduction of air the conversion rate of hydroxyacetone can be increased this teaching is clearly restricted to introduction of air into the aqueous phase containing hydroxyacetone after the aqueous phase has been separated from the organic product phase. Thus in the process of Vasileva et al. the cleavage product will not come into contact with oxygen. Without wanted to be bound by theory it is believed, especially when interpreting the teaching of Vasileva et al., that the oxygen will oxidize hydroxyacetone thereby increasing rate and efficiency of hydroxyacetone conversion. Consequently it had to be expected, that if oxygen-containing gases are brought into contact with the cleavage product, what is strictly avoided according to the teaching of Vasileva et al., valuable products will likewise be degraded by oxidation reactions resulting in a loss of overall selectivity and yield.

The present inventors have now surprisingly discovered, that contrary to the above expectations the introduction of oxygen into the homogeneous phase of reaction product and aqueous base does not lead to a detectable degradation of valuable products, despite the fact that then valuable products will be in contact with oxygen. Thus, surprisingly the introduction of oxygen into the homogeneous phase of the reaction product does not negatively affect the selectivity of the overall process.

To achieve the desired affect of increasing rate of conversion of hydroxyacetone the amount of oxygen introduced into the homogeneous phase should correspond at least to the stoichiometric amount of hydroxyacetone present. Usually an excess of the stoichiometric amount is used. According to a preferred embodiment of the present invention the homogeneous phase of reaction product and aqueous base is saturated with the oxygen containing gas. If the amount of oxygen containing gas exceeds the saturation limit, a continuous liquid phase with gas bubbles dispersed therein is formed. Preferably, the oxygen-containing gas can be pressurized. A suitable pressure is within the range of 1 to 10 barabs.

Preferably the oxygen-containing gas is selected from oxygen and air. The advantage of using oxygen is, especially when saturating the homogeneous phase with oxygen, that no separate gas phase is formed, that has to be removed from the system in a separate purge gas stream.

The process of the invention can be integrated particularly advantageously into processes known hitherto for preparing phenols by:
a) acid-catalyzed cleavage of alkylaryl hydroperoxides and
b) thermal after-treatment of the cleavage product from step a), with the temperature in step b) being higher than in step a), since here the reaction product of the alkylaryl hydroperoxide cleavage is generally obtained at a temperature of at least 100° C. Consequently the reaction product has already the desired temperature to be processed according to the present invention or can be cooled to the desired temperature. In any event no additional energy for heating is necessary.

The process of the invention is suitable for the acid-catalyzed cleavage of one or more alkylaryl hydroperoxides (AAHPs), e.g., α-methylbenzene hydro-peroxide, α-methyl-p-methylbenzyl hydroperoxide, α,α-dimethylbenzyl hydroperoxide, also known as isopropylbenzene hydroperoxide or cumene hydroperoxide (CHP), α,α-methylethylbenzyl hydroperoxide, also known as sec-butylbenzene hydroperoxide, α,α-dimethyl-p-methylbenzyl hydroperoxide, α,α-dimethyl-p-ethylbenzyl hydroperoxide, α-methyl-α-phenylbenzyl hydroperoxide. The process of the invention is particularly useful for the acid-catalyzed cleavage of mixtures of alkylaryl hydroperoxides comprising at least cumene hydroperoxide (CHP). The process of the invention is very particularly preferably used for the cleavage of CHP.

In the following, the process of the invention will be described by way of example for the case of the acid-catalyzed cleavage of CHP into phenol and acetone, without the process of the invention being restricted to this embodiment.

Sulfuric acid is preferably used as catalyst for the cleavage of CHP. The cleavage product mixture preferably has sulfuric acid concentration of from 50 to 1000 wppm. It can be advantageous to alter the acid activity, i.e. the acid strength of the cleavage product, prior to the thermal treatment. The acid strength is dependent on the acid concentration and the concentration of water in the cleavage mixture. The higher the water content of the cleavage mixture, the more acid has to be added to the cleavage mixture to obtain the same acid activity, with the acid strength being inversely proportional to the square of the water concentration. Thus, for example, the acid strength of a cleavage mixture solution containing 200 wppm of sulfuric acid and 2% by weight of water is only one sixteenth of the acid strength of a cleavage mixture solution containing 200 wppm of sulfuric acid and 0.5% by weight of water.

The ideal acid strength and thus the ideal composition of the cleavage mixture in respect of acid concentration and water concentration can be determined by means of simple preliminary tests. In the case of cleavage mixtures having a water concentration of up to 6% by weight, a sulfuric acid concentration of from 100 to 500 wppm in the cleavage mixture has been found to be particularly advantageous. To increase the acid strength, it is usual to add further sulfuric acid. To reduce the acid strength, it is possible to add a base, e.g., a phenoxide solution, ammonia or sodium hydroxide solution, or water to the cleavage product. Preference is given to adding water to the cleavage product.

In a particularly preferred embodiment of the process of the invention, the cleavage product to be treated thermally has a CHP concentration which in combination with the concentrations of further compounds which react exothermically during the cleavage reaction liberates precisely that quantity of heat which will heat the cleavage product mixture to the desired temperature for the thermal after-treatment.

All the embodiments described in DE-A 100 21 482 and the reactors suitable for them can likewise be used in the process of the present invention. As an alternative, it is also possible, using a procedure analogous to that described in DE-A 100 51 581, to produce a mixture of a cleavage product from step a) and a concentrate comprising at least cumene hydroperoxide, dividing this mixture into at least two parts and feeding at least one of these parts to the acid-catalyzed cleavage of step a) and subjecting another of these parts to a thermal after-treatment according to step b) and setting the pH of the reaction product from step b) in accordance with the invention.

The at least two parts of the mixture are preferably treated so that one part is treated at a temperature of from 45 to 99°

C., preferably from 45 to 90° C., to bring about the cleavage of cumene hydroperoxide and another part is heated to temperatures above 100° C. to effect cleavage of cumene hydroperoxide. In the case of the part which is heated to temperatures above 100° C., cleavage of cumene hydroperoxide takes place together with an integrated thermal aftertreatment. This part is preferably treated at a temperature above 115° C., particularly preferably above 130° C. and very particularly preferably above 150° C., with this temperature resulting from the exothermic reaction occurring in this step.

The precise setting of the composition of the mixture which is subjected to the high-temperature cleavage or the thermal after-treatment in order to obtain a desired temperature is described in detail in DE-A 100 51 581. The relevant disclosure of that patent publication is hereby incorporated by reference. Furthermore, all embodiments described in DE-A 100 51 581 and the reactors suitable for them can also be used in the process of the present invention.

It is assumed, without being tied to a theory, that the hydroxyacetone and other carbonyl functional by-products formed in the cleavage reaction react due to the presence of a basic compound in homogeneous phase according to the invention to form condensation products and/or if oxygen is present to oxidation products, which can easily be separated off from the product mixture. Furthermore, suppresses acid-catalyzed secondary reactions, including the reaction of hydroxyacetone with phenol, which lead to yield losses of phenol and can continue to take place during the cooling phase are suppressed. The process of the invention thus leads, in a simple manner, both to simplified removal of by-products and to an improvement in the selectivity, since hydroxyacetone is removed by reaction from the cleavage product and at the same time the undesirable reaction of hydroxyacetone with phenol, inter alia, is suppressed.

To enable the process of the invention, in particular the removal of hydroxyacetone and other by-products from the cleavage product by reaction of the byproducts to form condensation products, to be controlled more readily, it can be advantageous to introduce the cleavage product into a residence time vessel after the addition of the aqueous base and prior to cooling. Depending on the temperature chosen, a residence time in the range 10–7200 seconds, preferably 10–3600 seconds, can be set, with the residence time decreasing with increasing temperature of the cleavage product.

The process of the invention makes it possible to obtain a mixture comprising phenol and acetone in which the hydroxyacetone content does not exceed 400 wppm, preferably 300 wppm, particularly preferably 200 wppm and very particularly preferably 100 wppm.

In working-up after the treatment of the present invention the cleavage product is optionally cooled then neutralized and fractionated. These steps are known per se to a person skilled in the art and are not critical to the present invention, so that a more precise description is not necessary.

The merits of the process of the invention are illustrated by the examples below.

COMPARATIVE EXAMPLE 1

A cleavage product was produced from 70% strength by weight cumene hydroperoxide. The cleavage product was cooled to 40° C. and subsequently neutralized (pH=7). The cleavage product comprised 42 wt.-% phenol, 26 wt.-% acetone, 3.1 wt.-% alpha-methylstyrene, and 1200 wppm hydroxyacetone besides other organic components. All concentrations are related to the total amount of organic components (water-free). In addition, 1 wt. % of water is present.

COMPARATIVE EXAMPLE 2

The cleavage product of comparative example I was combined with 1.5% of an aqueous sodium phenolate solution (42% sodium phenolate) and water in an amount to obtain a two-phase mixture with 90 vol.-% of organic phase and 10 vol.-% of aqueous phase. The pH of the aqueous phase was about 10.5. The two phases were vigorously mixed at 120° C. for 2 h. The cleavage product comprised 42 wt.-% phenol, 26 wt.-% acetone, 3.1 wt.-% alpha-methylstyrene, and 755 wppm hydroxyacetone besides other organic components. All concentrations are related to the total amount of organic components (water-free).

EXAMPLE 1

The comparative example 1 was repeated with the difference that in the cleavage product 1.0 wt.-% sodium phenolate were dissolved. The sodium phenolate was added by means of 42 wt.-% aqueous sodium phenolate solution, whereby the water content of the cleavage product was increased to 2.4 wt.-%. The mixture of cleavage product and aqueous phenolate solution remained homogeneous. The homogeneous mixture was saturated with air by applying air at a pressure of 3 barabs. The mixture was held for 2 hours at 80° C. under constant air pressure. The cleavage product comprised 42 wt.-% phenol, 26 wt.-% acetone, 3.1 wt.-% alpha-methylstyrene, and 300 wppm hydroxyacetone. All concentrations are related to the total amount of organic components (water-free).

EXAMPLE 2

The comparative example 1 was repeated with the difference that in the cleavage product 1.5 wt.-% sodium phenolate were dissolved. The sodium phenolate was added by means of 42 wt.-% aqueous sodium phenolate solution, whereby the water content of the cleavage product was increased to 3.1 wt.-%. The mixture of cleavage product and aqueous phenolate solution remained homogeneous. The homogeneous mixture was saturated with air by applying air at a pressure of 5 barabs. The mixture was held for 2 hours at 80° C. under constant air pressure. The cleavage product comprised 42 wt.-% phenol, 26 wt.-% acetone, 3.1 wt.-% alpha-methylstyrene, and less than 50 wppm hydroxyacetone. All concentrations are related to the total amount of organic components (water-free).

When comparing the examples of the present invention with the comparative examples it becomes evident, that the content of hydroxyacetone can be considerably reduced without compromising selectivity and yield of the desired products phenol, acetone and alpha-methylstyrene.

What is claimed is:

1. A method for preparing phenols comprising:
    adding an aqueous base to a reaction product from an acid-catalyzed cleavage of alkylaryl hydroperoxides while maintaining a homogeneous phase prior to work-up of the product, and
    introducing an oxygen-containing gas into the reaction product.

2. The method of claim 1, wherein the aqueous base is selected from the group consisting of aqueous NaOH and aqueous phenoxide solutions.

3. The method of claim 2, wherein the aqueous base is an aqueous phenoxide solution recovered from at least one working-up stage of the process for preparing phenols.

4. The method of claim 2, wherein the phenoxide is sodium phenolate, and wherein the aqueous sodium phenolate solution or the aqueous NaOH solution is added to the reaction product in a concentration and amount to result in an sodium phenolate concentration in the homogeneous phase of 0.2 to 2.5 wt.-%.

5. The method of claim 4, wherein the sodium phenolate concentration in the homogeneous phase is between 0.5 and 1 wt.-%.

6. The method of claim 1, further comprising adjusting the temperature of the homogeneous phase after addition of the aqueous base to a temperature in the range of 20° C. to 150° C.

7. The method of claim 6, wherein said temperature is in the range of 60° C. to 120° C.

8. The method of claim 6, wherein said temperature is in the range of 80° C. to less than 100° C.

9. The method of claim 1, wherein the reaction product is saturated with the oxygen-containing gas.

10. The method of claim 1, wherein the oxygen-containing gas is pressurized.

11. The method of claim 1, wherein the oxygen-containing gas is selected from the group consisting of oxygen and air.

12. The method of claim 1, wherein the homogeneous phase comprising the reaction product and the aqueous base is maintained in a residence time vessel prior to work-up of the product.

13. The method of claim 12, wherein the residence time is between about 10 and about 7200 seconds.

14. The method of claim 1, wherein the alkylaryl hydroperoxide is cumene hydroperoxide.

15. The method of claim 1, further comprising work-up of the product wherein the work-up of the reaction product comprises:
neutralizing the reaction product, and
fractionating the reaction product.

16. The method of claim 15, further comprising cooling the reaction product prior to neutralizing.

* * * * *